(12) United States Patent
Iwaki et al.

(10) Patent No.: US 7,541,168 B2
(45) Date of Patent: Jun. 2, 2009

(54) RECOMBINANT CYCLOPENTANONE MONOOXYGENASE [CPMO]

(75) Inventors: Hiroaki Iwaki, Montreal (CA); Yoshie Hasegawa, Higashi-Osaka (JP); Peter C. K. Lau, Kirkland (CA)

(73) Assignee: National Research Council of Canada, Ontario (CA)

( * ) Notice: Subject to any disclaimer, the term of this patent is extended or adjusted under 35 U.S.C. 154(b) by 0 days.

(21) Appl. No.: 11/727,730

(22) Filed: Mar. 28, 2007

(65) Prior Publication Data

US 2007/0178558 A1    Aug. 2, 2007

Related U.S. Application Data

(62) Division of application No. 10/312,585, filed as application No. PCT/CA01/01032 on Jul. 13, 2001, now Pat. No. 7,214,520.

(60) Provisional application No. 60/218,842, filed on Jul. 18, 2000.

(51) Int. Cl.
    C12N 9/02    (2006.01)
    C07H 21/04   (2006.01)

(52) U.S. Cl. ..................... 435/189; 536/23.2

(58) Field of Classification Search ........... 435/189, 435/6, 69.1, 320.1, 252.33; 536/23.2
    See application file for complete search history.

(56) References Cited

U.S. PATENT DOCUMENTS

| | | | |
|---|---|---|---|
| 5,017,495 A | 5/1991 | Yen et al. |
| 5,079,166 A | 1/1992 | Winter et al. |
| 5,114,852 A | 5/1992 | Yabusaki et al. |
| 5,171,684 A | 12/1992 | Yen et al. |
| 5,605,823 A | 2/1997 | Yen et al. |
| 5,916,791 A | 6/1999 | Hirschberg et al. |
| 5,928,921 A | 7/1999 | Hayashi et al. |
| 5,942,426 A | 8/1999 | Hayashi et al. |
| 5,965,795 A | 10/1999 | Hirschberg et al. |
| 6,100,446 A | 8/2000 | Streber et al. |
| 6,140,512 A | 10/2000 | Adger et al. |
| 6,153,401 A | 11/2000 | Streber et al. |
| 6,218,599 B1 | 4/2001 | Hirschberg et al. |

FOREIGN PATENT DOCUMENTS

| | | |
|---|---|---|
| EP | 86139 | 8/1983 |
| EP | 247600 | 12/1987 |
| EP | 725137 | 8/1996 |
| EP | 999274 | 5/2000 |
| EP | 1006191 | 6/2000 |
| JP | 62-228276 | 10/1987 |
| JP | 1-074983 | 3/1989 |
| JP | 2-119777 | 5/1990 |
| JP | 9-121864 | 5/1997 |
| JP | 10-099078 | 4/1998 |
| WO | WO 98/24914 | 6/1998 |
| WO | WO 98/38294 | 9/1998 |
| WO | WO 98/46762 | 10/1998 |
| WO | WO 00/09682 | 2/2000 |
| WO | WO 01/07629 | 2/2001 |
| WO | WO 01/07630 | 2/2001 |
| WO | WO 01/11026 | 2/2001 |
| WO | WO 01/14574 | 3/2001 |
| WO | WO 01/20011 | 3/2001 |
| WO | WO 01/31047 | 5/2001 |
| WO | WO 01/36654 | 5/2001 |
| WO | WO 01/38500 | 5/2001 |

OTHER PUBLICATIONS

Bes et al. Oxidative biotransformations by microorganisms: production of chiral synthons by cyclopentanone monooxygenase from Pseudomonas sp. NCIMB 9872, J Molecular Catalysis B: Enzymatic, 1(3): 127-134, 1996.*
Chen et al. (Acinetobacter cyclohexanone monooxygenase: gene cloning and sequence determination, J Bacteriol. Feb. 1988; 170(2): 781-9.*
Altschul et al., 1997, Nucleic Acids Res., 25 : 3389-3402.
Birnboim and Doly, 1979, DNA Nucleic Acids Res., 7 : 1513-1523.
Bradford, 1976, Anal. Biochem., 72: 248-254.
Cha et al., 1993, Gene, 136: 369-370.
Chen et al., 1988, J. Bacteriol., 170: 781-789.
Donoghue et al., 1976, Eur. J. Biochem., 63: 175-192.
Enroth et al., 1998, Structure, 6 : 605-617.
Eppink et al., 1997, Prot. Sci., 6: 2454-2458.
Griffin et al., 1972, Biochem J., 129: 595-603.
Griffin et al., 1976, Eur. J. Biochem., 63 : 199-209.
Jornvall et al., 1995, Biochemistry, 34: 6003-6013.
Kokotek et al., 1989, Gene, 84: 467-471.
Kruger et al., 1992, J. Bacteriol., 179: 4391-4400.
Marmur, 1961, J. Mol. Biol., 3: 208-218.
Miranda et al., 1987, The complete nucleotide sequence of the gInALG operon of Eschericha coli K12, 15: 2757-2770.
Morett and Segovia, 1993, J. Bacteriol., 175: 6067-6074.
Morii et al., 1998, GenBank accession No. AB010439.
Sambrook et al., 1989, Molecular cloning: a laboratory manual, 2nd ed., Cold Spring Harbor Laboratory Press, Cold Spring Harbor, N.Y.

(Continued)

Primary Examiner—Nashaat T Nashed
Assistant Examiner—Iqbal H Chowdhury
(74) Attorney, Agent, or Firm—Ogilvy Renault LLP

(57) ABSTRACT

Cyclopentanone 1,2-monooxygenase (CPMO) from *Comamonas* (previously *Pseudomonas*) sp. strain NCIMB 9872 carries out the second step of a degradation pathway that allows the bacterium to use cyclopentanol as a sole carbon source for growth. In the present invention there is reported the localization of the CPMO-encoding gene (cpnB) on a 4.3-kb SphI fragment, the determination of its sequence. The 550-amino acid CPMO polypeptide ($M_r$, 62,111) encoded by the gene was found to have 36.5% identity with the sequence of cyclohexanone 1,2-monooxygenase (CHMO) of *Acinetobacter* sp. strain NCIMB 9871. The 62-kDa CPMO was expressed in *E. coli* as an IPTG-inducible protein.

4 Claims, 10 Drawing Sheets

OTHER PUBLICATIONS

Smith et al., 1996, Biochemistry, 35: 8805-8814.
Stewart, 1998, Curr. Org. Chem., 2: 195-216.
Stewart et al., 1998, J. Am. Chem. Soc., 120 : 3541-3548.
Stinson, 1998, Chem. Eng. News., 83-104.
Willetts, 1997, Trends in Biotech., 15: 55-62.
Yanisch-Perron et al., 1985, Gene, 33: 103-119.

* cited by examiner

```
                                         GxGxxG
SEQ ID NO: 7  CHMO    1:---------------MSQKMDFDAIVIGGGFGGLYAVKKLRDELELKVQAFDKATDVAGT  45
SEQ ID NO: 6  STMO    1:MNGQHPRSVVTAPDATTGTTSYDVVVVGAGIAGLYAIHRFRSQ-GLTVRAFEAASGVGGV  59
SEQ ID NO: 5  CPMO    1:MTTMTTMTTEQLGMNNSVNDKLDVLLIGAGFTGLYQLYHLRKL-GYKVHLVDAGADIGGI  59
                            *  ..* *, ***  ...*        *. .  . *

SEQ ID NO: 7  CHMO   46:WYWNRYPGALTDTETHLYCYSWDKELLQSLEIKKKYVQGPDVRKYLQQVAEKHDLKKSYQ 105
SEQ ID NO: 6  STMO   60:WYWNRYPGARCDVESIDYSYSFSPELEQEWNWSEKYATQPEILAYLEHVADRFDLRRDIR 119
SEQ ID NO: 5  CPMO   60:WHWNCYPGARVDTHCQIYQYSI-PELWQEFNWKELFPNWAQMREYFHFADKKLDLSKDIS 118
                        *.** ****  *     *  **  ** *   . .   ..  *.    . **  .

SEQ ID NO: 7  CHMO  106:FNTAVQSAHYNEADALWEVTTEYGDKYTARFLITALGLLSAPNLPNIKGINQFKGELHHT 165
SEQ ID NO: 6  STMO  120:FDTRVTSAVLDEEGLRWTVRTDRGDEVSARFLVVAAGPLSNANTPAFDGLDRFTGDIVHT 179
SEQ ID NO: 5  CPMO  119:FNTRVQSAVFDEGTREWTVRSIGHQPIQARFVIANLGFGASPSTPNVDGIETFKGQWYHT 178
                        *.* * ** ,*    * **  .    * ***..    *   *   *   *.. * *. **
                                         GxGxxG
SEQ ID NO: 7  CHMO  166:SRWPDD-VSFEGKRVGVIGTGSTGVQVITAVAPLAKHLTVFQRSAQYSVPIGNDPLSEED 224
SEQ ID NO: 6  STMO  180:ARWPHDGVDFTGKRVGVIGTGSSGIQSIPIIAEQAEQLFVFQRSANYSIPAGNVPLDDAT 239
SEQ ID NO: 5  CPMO  179:ALWPQEGVNMAGKRVAIIGTGSSGVQVAQEAALDAKQVTVYQRTPNLALPMHQKQLSAED 238
                        . **   *   . **** ,*****.*.*        *  ,* ,**.  .  .  *   *

SEQ ID NO: 7  CHMO  225:VKKIKDNYDKSLGWCMNSALAFALNESTVPAMSVSAEERKAVFEKAWQTGGGFRFMFETF 284
SEQ ID NO: 6  STMO  240:RAEQKANYAERRRLSRESGGGSPHRPHPKSALEVSEEERRAVYEERWKLGG--VLFSKAF 297
SEQ ID NO: 5  CPMO  239:NLRMKPELPAAFERRGKCFAGFDFDFIAKNATELSAAERTEILEELWNAGG-FRYWLANF 297
                         *  .     .      * .*  ** . . * **  . *. * **          *
```

FIG. 3A

```
SEQ ID NO:7 CHMO 285:GDIATNMEANIEAQNFIKGKIAEIVKDPAIAQKLMPQD----LYAKRPLCDSGYYNTFNR 340
SEQ ID NO:6 STMO 298.PDQLTDPAANDTARAFWEEKIRAVVDDPAVAELLTPKDH--AIGAKRIVTDSGYYETYNR 355
SEQ ID NO:5 CPMO 298:QDYLFDDKANDYVYEFWRDKVRARIKDPKVAEKLAPMKKPHPYGAKRPSLEQWYYEIFNQ 357
                   .   ** .  *  *.  .**  .*  *  *       ***   **  .*.

SEQ ID NO:7 CHMO 341.DNVRLEDVKANPIVEITENGVKLENGDFVELDMLICATGFDAVDGNYVRMDIQGKNGLAM 400
SEQ ID NO:6 STMO 356:DNVELVDLRSTPIVGMDETGIVT-TGAHYDLDMIVLATGFDAMTGSLDKLEIVGRGGRTL 414
SEQ ID NO:5 CPMO 358:NNVTLVDVNETPVLRITEKGIVT-AEGEAEFDLIVFATGFDAVTGGITSIDFRNNQGQSF 416
                     .** * *.  *...* *.       ..*... ******. *   ...  *  ..

SEQ ID NO:7 CHMO 401:KDYWKEGPSSYMGVTVNNYPNMFMVLGPNGP--FTNLPPSIESQVEWISDTIQYTVENNV 458
SEQ ID NO:6 STMO 415:KETWAAGPRTYLGLGIDGFPNFFNLTGPGSPSVLANMVLHSELHVDWVADAIAYLDARGA 474
SEQ ID NO:5 CPMO 417:KDVWSDGIRTQLGVATAGFPNLLFGYGPQSPAGFCNGPSSAEYQGDLLIQLMNYLRDNNI 476
                    *. * *  . .*.  .**.. ** * .*     *......*

SEQ ID NO:7 CHMO 459:ESIEATKEAEEQWTQTCANIAEMTLFPKAQSWIFGANIPGKKNTVYFYLGGLKEYRTCAS 518
SEQ ID NO:6 STMO 475:AGIEGTPEAVADWVEECRNRAEASLLNSANSWYLGANIPGRPRVFMPFLGGFGVYREIIT 534
SEQ ID NO:5 CPMO 477:SRIEAQSEAQEEWSKLIADFWDSSLFPRAKSWYQGSNIPGKKVESLNFPLGLPTYISKFN 536
                     * ** .* .   ..*. *.** *.**** .      *. *

SEQ ID NO:7 CHMO 519:NCKNHAYEGFDIQLQRSDIKQPANA 543
SEQ ID NO:6 STMO 535:EVAESGYKGFAILEG---------- 549
SEQ ID NO:5 CPMO 537:ESAEKGYAGFSLAS----------- 550
                       .  * **  .
```

FIG. 3B

```
              10        20        30        40        50        60
               |         |         |         |         |         |
  1   GCATGCGATAGCGGCACGTTGGTGGGCGGGCGAGCGCGGCCACGAGCGCGTCTCTCGCTC
      CGTACGCTATCGCCGTGCAACCACCCGCCCGCTCGCGCCGGTGCTCGCGCAGAGAGCGAG
 61   CACCGACATCACATCGCCGGTCACCGGCGAGAACATTGGCAAGATCCTGCGCTTTTCGCC
      GTGGCTGTAGTGTAGCGGCCAGTGGCCGCTCTTGTAACCGTTCTAGGACGCGAAAAGCGG
121   GCTGAAGCCGCAGGGCTACGAGAGAATTTTTCAGTCCGGCCTGGCGGACTCGACCCAGCA
      CGACTTCGGCGTCCCGATGCTCTCTTAAAAAGTCAGGCCGGACCGCCTGAGCTGGGTCGT
181   CACCCCCAGGATGGTGCGTTTCGGACAGTTCCTGTCCTGTGATCCAGAGACCATCAACAC
      GTGGGGGTCCTACCACGCAAAGCCTGTCAAGGACAGGACACTAGGTCTCTGGTAGTTGTG
241   CCTGGAGACATTGGAGCGGATCGCGCGCGCCGACGTCAATGTCTTGCTGCATGGAGAGAC
      GGACCTCTGTAACCTCGCCTAGCGCGCGGCTGCAGTTACAGAACGACGTACCTCTCTG
301   GGGCACGGGCAAAGAGCTGATAGCTCGCCACATTCATGTCGCGAGCCGCCGGCGGGATGC
      CCCGTGCCCGTTTCTCGACTATCGAGCGGTGTAAGTACAGCGCTCGGCGGCCGCCCTACG
361   GCCCTACCTCGCCATCAACTGCGGGGCAATCAGCTCGGAGTTGCTGGAGAGTACTTTTTT
      CGGGATGGAGCGGTAGTTGACGCCCCGTTAGTCGAGCCTCAACGACCTCTCATGAAAAAA
421   TGGCTATGTGCGCGGAGCATTCTCCGGGGCAGATCCCAAGGGCCGCGCCGGCTACTTTGA
      ACCGATACACGCGCCTCGTAAGAGGCCCCGTCTAGGGTTCCCGGCGCGGCCGATGAAACT
481   ATCGGTGGGCGAAGGCACCTTGTTTCTGGACGAGATCGGCGAGCTGCCCTTGGCCATGCA
      TAGCCACCCGCTTCCGTGGAACAAAGACCTGCTCTAGCCGCTCGACGGGAACCGGTACGT
541   GGCGGCATTGTTGCGCGTGCTGGAAGACGGAAGCTTTCTGCGTGTGGGCTCATCGACCCC
      CCGCCGTAACAACGCGCACGACCTTCTGCCTTCGAAAGACGCACACCCGAGTAGCTGGGG
601   GCAGCGCGCCTCGTGCCGCATTATCGCGGCCACGCACCGCAATCTGGAGGAACTCATCGC
      CGTCGCGCGGAGCACGGCGTAATAGCGCCGGTGCGTGGCGTTAGACCTCCTTGAGTAGCG
661   ACAGGGCCTGTTTCGCCAGGATCTCTACTACCGTCTCAAGATCGTTCAGAAAAGGCTCAA
      TGTCCCGGACAAAGCGGTCCTAGAGATGATGGCAGAGTTCTAGCAAGTCTTTTCCGAGTT
```

FIG. 5A

```
 721 GCCGATACGGGAACGCACCTGTGACATCGCCTTGCTGGCAGAGCAATTCAAATCTGCACT
     CGGCTATGCCCTTGCGTGGACACTGTAGCGGAACGACCGTCTCGTTAAGTTTAGACGTGA
 781 GGCGCAAAAGCACCAGATCCCGAACGTGCAGATCCACCCCGAGGCCATGGCAGTCATGGA
     CCGCGTTTTCGTGGTCTAGGGCTTGCACGTCTAGGTGGGGCTCCGGTACCGTCAGTACCT
 841 GCGCTACCAGTGGCCGGGCAATGCGCGCGAAATCCGCAATGTGATGGAAGCCGCCCTGAT
     CGCGATGGTCACCGGCCCGTTACGCGCGCTTTAGGCGTTACACTACCTTCGGCGGGACTA
 901 CTGCTCCGATGGTGAAATCACGCTCGCCAGCCTGCCCCCGGAAGTATCTGAGAACTCCAC
     GACGAGGCTACCACTTTAGTGCGAGCGGTCGGACGGGGGCCTTCATAGACTCTTGAGGTG
 961 CTATCCTCTGCAAAGCCGGGTGGCCGAAGCGAATAGCGAGATGCCTCCCGTCTCCGGCAA
     GATAGGAGACGTTTCGGCCCACCGGCTTCGCTTATCGCTCTACGGAGGGCAGAGGCCGTT
1021 CGACTATGAACGGCAACTCATCGTGGGTTTGCTGCGCAAGTACCGAAAGGTCAATCATGT
     GCTGATACTTGCCGTTGAGTAGCACCCAAACGACGCGTTCATGGCTTTCCAGTTAGTACA
1081 GGCGAGGGCCCTGGGCCTCGCGCGCTCCACGCTCTATCGGAAATTCGCAGACTTGGGCAT
     CCGCTCCCGGGACCCGGAGCGCGCGAGGTGCGAGATAGCCTTTAAGCGTCTGAACCCGTA
1141 TGACCAACGCGAGTATGTCAATGATCTGTCCGATTAACACTGCTGCGCCCTGCGCTTGCG
     ACTGGTTGCGCTCATACAGTTACTAGACAGGCTAATTGTGACGACGCGGGACGCGAACGC
1201 GCAACGCAGTATCGTCGGAACGCGGGCAACGCTAAAGGCAGCCGCCGTCGGCATCGGTTG
     CGTTGCGTCATAGCAGCCTTGCGCCCGTTGCGATTTCCGTCGGCGGCAGCCGTAGCCAAC
1261 CCGCCCGGTGTTGTTTGTCGGCTGAGACCGCCTGCAGCACCAGCCCCTCCATTCCTCGTG
     GGCGGGCCACAACAAACAGCCGACTCTGGCGGACGTCGTGGTCGGGGAGGTAAGGAGCAC
1321 TCTAGATCTCCTTGCAACGCTGTCACAGCGTGCTTTTTTCGTGGCGCGGGACTTCTCGCG
     AGATCTAGAGGAACGTTGCGACAGTGTCGCACGAAAAAAGCACCGCGCCCTGAAGAGCGC
1381 ATGAGGGCCTGCAAGGGCGGCGCATCAAAACAAGCGCCCTGTCCTCAGGACGTTTGCGCC
     TACTCCCGGACGTTCCCGCCGCGTAGTTTTGTTCGCGGGACAGGAGTCCTGCAAACGCGG
1441 GTCGCTGGCTATGGGCAGTCTGCATGATCCGCTTGGGCTTGCCCACCATGCGCGCGACTG
```

FIG. 5B

```
            CAGCGACCGATACCCGTCAGACGTACTAGGCGAACCCGAACGGGTGGTACGCGCGCTGAC
       1501 CGCTCTTTCCTGTTGGGCGCATCGTCATCCCGACCTTCCTGAAATCCATTTCCACAGGGC
            GCGAGAAAGGACAACCCGCGTAGCAGTAGGGCTGGAAGGACTTTAGGTAAAGGTGTCCCG
       1561 CGGCCTGAGCCAGACAGCGATCGGCAGGCTCTCGCATCTCGGACAGTGGTGCGCTACACC
            GCCGGACTCGGTCTGTCGCTAGCCGTCCGAGAGCGTAGAGCCTGTCACCACGCGATGTGG
       1621 ACAGGACACAAGTGTCCGGCGCGTGGCACGCAGCGGCCTTTGCTGCGCACGATGCGTGCT
            TGTCCTGTGTTCACAGGCCGCGCACCGTGCGTCGCCGGAAACGACGCGTGCTACGCACGA
       1681 TTTGGCACATGGAAACCCTCGGTTTTCCGAACCAGAGACCTGGCACAAGTCTTGATAAC
            AAACCGTGTACCTTTGGGAGCCAAAAAGGCTTGGTCTCTGGACCGTGTTCAGAACTATTG
       1741 TCCTGAGTGACTGATGCAACGCATCTCAGTCCGGGAGCGTGGACGACACGCCCCTGAACT
            AGGACTCACTGACTACGTTGCGTAGAGTCAGGCCCTCGCACCTGCTGTGCGGGGACTTGA
       1801 TCAATTATTTAGGAGACCCATATGACCACCATGACCACCATGACCACCGAACAACTCGGC
            AGTTAATAAATCCTCTGGGTATACTGGTGGTACTGGTGGTACTGGTGGCTTGTTGAGCCG
       1861 ATGAACAACTCTGTCAATGACAAGCTTGACGTTTTGCTCATCGGCGCCGGCTTCACCGGT
            TACTTGTTGAGACAGTTACTGTTCGAACTGCAAAACGAGTAGCCGCGGCCGAAGTGGCCA
       1921 CTCTACCAGCTCTATCACCTGCGCAAGCTGGGCTACAAGGTTCATCTCGTCGACGCCGGT
            GAGATGGTCGAGATAGTGGACGCGTTCGACCCGATGTTCCAAGTAGAGCAGCTGCGGCCA
       1981 GCCGATATTGGCGGGATCTGGCATTGGAACTGCTACCCCGGAGCGCGTGTGGATACCCAC
            CGGCTATAACCGCCCTAGACCGTAACCTTGACGATGGGGCCTCGCGCACACCTATGGGTG
       2041 TGCCAGATCTACCAGTACTCCATTCCAGAGTTGTGGCAGGAGTTCAACTGGAAAGAGCTG
            ACGGTCTAGATGGTCATGAGGTAAGGTCTCAACACCGTCCTCAAGTTGACCTTTCTCGAC
       2101 TTCCCTAACTGGGCGCAAATGCGCGAGTATTTCCATTTTGCCGACAAGAAGCTCGACCTG
            AAGGGATTGACCCGCGTTTACGCGCTCATAAAGGTAAAACGGCTGTTCTTCGAGCTGGAC
       2161 AGCAAGGACATCAGCTTCAACACCCGTGTGCAGTCGGCCGTCTTTGACGAAGGCACACGC
            TCGTTCCTGTAGTCGAAGTTGTGGGCACACGTCAGCCGGCAGAAACTGCTTCCGTGTGCG
```

FIG. 5C

2221 GAATGGACGGTACGCTCGATCGGACACCAGCCGATCCAGGCCAGGTTCGTCATCGCCAAC
     CTTACCTGCCATGCGAGCTAGCCTGTGGTCGGCTAGGTCCGGTCCAAGCAGTAGCGGTTG
2281 CTTGGCTTCGGTGCCAGCCCCAGCACGCCCAATGTCGATGGCATCGAGACATTCAAAGGC
     GAACCGAAGCCACGGTCGGGGTCGTGCGGGTTACAGCTACCGTAGCTCTGTAAGTTTCCG
2341 CAGTGGTATCACACTGCTCTGTGGCCCCAGGAAGGCGTGAACATGGCCGGCAAGCGCGTG
     GTCACCATAGTGTGACGAGACACCGGGGTCCTTCCGCACTTGTACCGGCCGTTCGCGCAC
2401 GCCATCATTGGCACCGGCTCCAGCGGGGTCCAGGTCGCCCAGGAGGCTGCCCTTGATGCG
     CGGTAGTAACCGTGGCCGAGGTCGCCCCAGGTCCAGCGGGTCCTCCGACGGGAACTACGC
2461 AAACAGGTGACGGTGTACCAGCGCACCCCCAACCTGGCCTTGCCCATGCATCAGAAGCAG
     TTTGTCCACTGCCACATGGTCGCGTGGGGGTTGGACCGGAACGGGTACGTAGTCTTCGTC
2521 CTCAGCGCCGAGGACAATCTGCGCATGAAGCCCGAGCTTCCCGCAGCGTTCGAGAGACGC
     GAGTCGCGGCTCCTGTTAGACGCGTACTTCGGGCTCGAAGGGCGTCGCAAGCTCTCTGCG
2581 GGCAAGTGCTTCGCCGGCTTCGACTTCGACTTCATCGCCAAGAACGCGACCGAGCTGTCC
     CCGTTCACGAAGCGGCCGAAGCTGAAGCTGAAGTAGCGGTTCTTGCGCTGGCTCGACAGG
2641 GCTGCGGAGCGCACAGAGATCTTGGAAGAGCTGTGGAACGCCGGCGGCTTCCGCTACTGG
     CGACGCCTCGCGTGTCTCTAGAACCTTCTCGACACCTTGCGGCCGCCGAAGGCGATGACC
2701 CTGGCCAATTTCCAAGACTATCTGTTCGATGACAAGGCCAACGATTACGTCTACGAGTTC
     GACCGGTTAAAGGTTCTGATAGACAAGCTACTGTTCCGGTTGCTAATGCAGATGCTCAAG
2761 TGGCGCGACAAGGTCCGCGCCCGCATCAAGGATCCGAAAGTTGCCGAGAAGCTCGCCCCC
     ACCGCGCTGTTCCAGGCGCGGGCGTAGTTCCTAGGCTTTCAACGGCTCTTCGAGCGGGGG
2821 ATGAAGAAGCCGCATCCTTACGGAGCCAAGCGCCCTTCGCTGGAGCAGTGGTACTACGAG
     TACTTCTTCGGCGTAGGAATGCCTCGGTTCGCGGGAAGCGACCTCGTCACCATGATGCTC
2881 ATCTTCAATCAGAACAACGTCACGCTGGTGGATGTCAACGAAACACCGGTGCTTCGCATC
     TAGAAGTTAGTCTTGTTGCAGTGCGACCACCTACAGTTGCTTTGTGGCCACGAAGCGTAG
2941 ACCGAGAAAGGCATCGTGACCGCTGAGGGTGAAGCCGAATTCGACCTGATCGTGTTCGCG

```
      TGGCTCTTTCCGTAGCACTGGCGACTCCCACTTCGGCTTAAGCTGGACTAGCACAAGCGC
3001  ACCGGCTTCGACGCAGTGACCGGGGGACTCACCAGCATCGACTTCCGCAACAACCAGGGC
      TGGCCGAAGCTGCGTCACTGGCCCCCTGAGTGGTCGTAGCTGAAGGCGTTGTTGGTCCCG
3061  CAGAGCTTCAAGGATGTGTGGTCTGACGGAATCCGCACCCAGCTGGGAGTGGCCACGGCA
      GTCTCGAAGTTCCTACACACCAGACTGCCTTAGGCGTGGGTCGACCCTCACCGGTGCCGT
3121  GGTTTTCCCAACTTGCTCTTTGGCTACGGACCTCAATCGCCTGCGGGCTTCTGCAACGGT
      CCAAAAGGGTTGAACGAGAAACCGATGCCTGGAGTTAGCGGACGCCCGAAGACGTTGCCA
3181  CCGTCGAGCGCCGAATACCAGGGCGATCTGCTGATCCAGCTGATGAACTACCTACGCGAC
      GGCAGCTCGCGGCTTATGGTCCCGCTAGACGACTAGGTCGACTACTTGATGGATGCGCTG
3241  AACAACATCTCGCGCATCGAAGCCCAGTCCGAGGCACAGGAAGAATGGAGCAAGCTGATC
      TTGTTGTAGAGCGCGTAGCTTCGGGTCAGGCTCCGTGTCCTTCTTACCTCGTTCGACTAG
3301  GCAGACTTCTGGGACAGCTCGCTGTTCCCCCGCGCAAAGTCCTGGTACCAAGGATCCAAC
      CGTCTGAAGACCCTGTCGAGCGACAAGGGGGCGCGTTTCAGGACCATGGTTCCTAGGTTG
3361  ATCCCGGGCAAGAAAGTCGAGAGCCTGAACTTCCCGCTGGGGCTGCCAACCTATATATCC
      TAGGGCCCGTTCTTTCAGCTCTCGGACTTGAAGGGCGACCCCGACGGTTGGATATATAGG
3421  AAATTCAATGAAAGCGCTGAAAAGGATATGCAGGCTTCTCGCTGGCCAGCTAAGACTCT
      TTTAAGTTACTTTCGCGACTTTTTCCTATACGTCCGAAGAGCGACCGGTCGATTCTGAGA
3481  GTTGTGCAACTCCTGGAGACAAGCATATGGGACGTGTAAATGACAAAGTGGTTCTCGTCA
      CAACACGTTGAGGACCTCTGTTCGTATACCCTGCACATTTACTGTTTCACCAAGAGCAGT
3541  CTGGCGGTGCCATGGGAATGGGCCTGACCCATTGCACCTTGCTGGCCCGCGAGGGGGCCA
      GACCGCCACGGTACCCTTACCCGGACTGGGTAACGTGGAACGACCGGGCGCTCCCCCGGT
3601  CCGTTTACCTCAGCGACATGAATGAGGAACTGGGCCACCAAGCCGTAGCGGAGATCCGTC
      GGCAAATGGAGTCGCTGTACTTACTCCTTGACCCGGTGGTTCGGCATCGCCTCTAGGCAG
3661  GGCAAGGTGGCAAGGCCCACTTCCTGCACCTGGACGTGACCAACGAGAATCACTGGACAG
      CCGTTCCACCGTTCCGGGTGAAGGACGTGGACCTGCACTGGTTGCTCTTAGTGACCTGTC
```

FIG. 5E

3721 GTGCCGTGGACACCATCCTCGCCGAGTCCGACCGGCTGGACGCGCTGGTCAACAACGCCG
     CACGGCACCTGTGGTAGGAGCGGCTCAGGCTGGCCGACCTGCGCGACCAGTTGTTGCGGC
3781 GCATTTTGACCCTCAAACCCGTTCAGGACACCAGCAACGAAGAATGGGATCGCATCTTTG
     CGTAAAACTGGGAGTTTGGGCAAGTCCTGTGGTCGTTGCTTCTTACCCTAGCGTAGAAAC
3841 AAATCAATGTCCGCAGTGTGTTCTTGGGCACGCGAGCAGTGATCGAGCCCATGCGTAAAG
     TTTAGTTACAGGCGTCACACAAGAACCCGTGCGCTCGTCACTAGCTCGGGTACGCATTTC
3901 CCCATAAAGGCTGCATCGTCAATGTGTCGTCCATCTACGGTCTGGTGGGTGCGCCGGGAG
     GGGTATTTCCGACGTAGCAGTTACACAGCAGGTAGATGCCAGACCACCCACGCGGCCCTC
3961 CTGCGGCCTACGAGGCCTCCAAAGGTGCCGTGCGCTTGTTTACCAAGGCTTGCGCGGTGG
     GACGCCGGATGCTCCGGAGGTTTCCACGGCACGCGAACAAATGGTTCCGAACGCGCCACC
4021 ACCTGGCACCGTTCAATATTCGGGTCAACTCGGTCCACCCAGGGGTGATCGCAACACCCA
     TGGACCGTGGCAAGTTATAAGCCCAGTTGAGCCAGGTGGGTCCCCACTAGCGTTGTGGGT
4081 TGACGCAGCAGATCCTGGACGCCCCACAGAGCGCACGTGCGCTTCTGGGCCCCACGCTGC
     ACTGCGTCGTCTAGGACCTGCGGGGTGTCTCGCGTGCACGCGAAGACCCGGGGTGCGACG
4141 TGGGTCGTGCGGCCCAGCCGATGGAGGTCTCCCAGGCGGTGCTTTTCCTGGTCTCGGACG
     ACCCAGCACGCCGGGTCGGCTACCTCCAGAGGGTCCGCCACGAAAAGGACCAGAGCCTGC
4201 AGGCCTCGTTCGTGCATGGCTCTGAACTCGTCGTCGACGGAGGGTATACGGCGAACTGAG
     TCCGGAGCAAGCACGTACCGAGACTTGAGCAGCAGCTGCCTCCCATATGCCGCTTGACTC
4261 AAAGGAACATCCTCGGCATGC
     TTTCCTTGTAGGAGCCGTACG

FIG. 5F

RECOMBINANT CYCLOPENTANONE MONOOXYGENASE [CPMO]

RELATED APPLICATIONS

The present application is a divisional application of U.S. Ser. No. 10/312,585 filed Oct. 23, 2003, now U.S. Pat. No. 7,214,520 issued May 8, 2007, which itself claims priority from U.S. Ser. No. 60/218,842, filed Jul. 18, 2000, now abandoned, and International Application Number PCT/CA01/01032, filed Jul. 13, 2001, now abandoned, each incorporated herein by reference in their entirety.

TECHNICAL FIELD

The present invention relates to an isolated DNA encoding a cyclopentanone monooxygenase (CPMO), or an enzymatically active portion thereof, and expression vector and a transformed cell containing the isolates DNA.

BACKGROUND OF THE INVENTION

*Comamonas* (previously *Pseudomonas*) sp. NCIMB 9872 was one of the few microorganisms that have been characterized to produce a Baeyer-Villiger monooxygenase (BVMO; Griffin, M., et al., *Biochem. J.* 129:595-603, 1972; Griffin, M., et al., *Eur. J. Biochem.* 63:199-209, 1976; and Willetts, A., *Trends in Biotech.* 15:55-62, 1997; for a recent review). BVMOs are flavoproteins that mimic the classical Baeyer-Villiger organic chemical reaction which is a peracid-catalyzed oxidation of a ketone to an ester or lactone. The use of enzyme substitutes for the production of lactones in high yield and optical purity is an attractive feature in current trends of research and development toward replacing chemical methods with biological alternatives (Stinson, S. C., *Chem. Eng. News*, 83-104, 1998). To date, the best characterized BVMO enzyme is that of cyclohexanone monooxygenase (CHMO) produced by *Acinetobacter* sp. NCIMB 9871 (Stewart, J. D., *Curr. Org. Chem.* 2:195-216, 1998; Willetts, A., *Trends in Biotech.* 15:55-62, 1997). This is also the only BVMO whose gene has been cloned and sequenced (Chen, et al., *J. Bacteriol.* 170:781-789, 1988). Recently, this valuable resource was used to engineer a "designer yeast" in a whole-cell approach to effect a variety of asymmetric Baeyer-Villiger oxidations (Stewart, J. D., et al., *J. Am. Chem. Soc.* 120:3541-3548, 1998).

It would be highly desirable to be provided with a new CPMO having an increased enzymatic activity for growing cells in a medium containing cyclopentanol or cyclopentanone as sole carbon source.

SUMMARY OF THE INVENTION

One aim of the present invention is to provide a new CPMO having an increased enzymatic activity for growing cells in a medium containing cyclopentanol or cyclopentanone as sole carbon source.

In accordance with the present invention there is provided an isolated DNA encoding a cyclopentanone monooxygenase (CPMO), or an enzymatically active portion thereof, the isolated DNA being characterized by the ability to hybridize specifically with the complement of the DNA represented in SEQ ID NO:8 under stringent hybridization conditions.

Also in accordance with the present invention, there is provided an isolated DNA, wherein it codes for a cyclopentanone monooxygenase (CPMO), and contains:

(1) the nucleic acid sequence of SEQ ID NO:8;
(2) a sequence corresponding to said nucleic acid sequence in the scope of the degeneration of the genetic code; or
(3) a sequence hybridizing under stringent conditions with the sequence from (1) or (2), and still coding for cyclopentanone monooxygenase (CPMO).

Still in accordance with the present invention, there is provided an isolated DNA encoding a cyclopentanone monooxygenase (CPMO), or an enzymatically active portion thereof, said isolated DNA having SEQ ID NO:8.

The present invention further provides an isolated DNA expression vector encoding an enzymatically active cyclopentanone monooxygenase (CPMO) comprising a DNA characterized by a sequence as set forth in SEQ ID NO:8, or a portion thereof, said portion encoding said CPMO, in expressible form.

In accordance with the present invention, there is also provided a recombinant vector comprising the isolated DNA as described above, wherein the isolated DNA encodes cyclopentanone monooxygenase.

In a preferred embodiment of the present invention, the isolated DNA has a nucleic acid sequence of SEQ ID NO:8 or which, due to the degeneracy of the genetic code, is a functional equivalent thereof.

Also in accordance with the present invention, there is provided a recombinant vector containing one or more copies of a recombinant DNA described above.

The recombinant vector may be a prokaryotic vector. The recombinant vector may also be a plasmid.

Therefore, in accordance with the present invention, there is also provided a biologically functional plasmid or viral DNA vector, which contains a DNA as described above.

The present invention also provide a host cell comprising a recombinant vector as described above.

Accordingly, there is also provided a cell transformed with a heterologous DNA expression construct encoding an enzymatically active cyclopentanone monooxygenase (CPMO) comprising a DNA characterized by a sequence as set forth in SEQ ID NO:8, or a portion thereof, said portion encoding said CPMO, in expressible form.

The cell may be a prokaryotic cell or it may be *E. coli*.

Still in accordance with the present invention, there is also provided a purified cyclopentanone monooxygenase (CPMO) having:
  a) an amino acid sequence as set forth in SEQ ID NO:5;
  b) an amino acid sequence encoded by a nucleic acid sequence as set forth in SEQ ID NO:8; or
  c) an amino acid sequence encoded by a nucleic acid sequence hybridizing to a nucleic acid sequence complementary to the nucleic acid sequence of step b) above under stringent conditions, said amino acid sequence encoded in step c) having a same activity as the amino acid sequence in a).

The present invention also provides a recombinant cyclopentanone monooxygenase (CPMO) having an enzymatic activity superior to the one from a native *Pseudomonas*, and more preferably twice superior.

The recombinant cyclopentanone monooxygenase (CPMO) may be prepared from *Comamonas* sp. NCIMB 9872. The recombinant cyclopentanone monooxygenase (CPMO) has preferably a sequence as set forth in SEQ ID NO:5.

A method for growing cells in vitro in presence of cyclopentanol or cyclopentanone as sole source of carbon, said method comprising the steps of:
  a) transforming a cell with the expression construct described above; and b) growing the cell of step a) under suitable conditions in a medium containing cyclopentanol or cyclopentanone as a sole source of carbon.

To increase this gene potential, according to the invention it is reported herein the cloning of a cyclopentanone monooxygenase (CPMO)-encoding gene (cpnB) from *Comamonas* (*Pseudomonas*) sp. NCIMB 9872, the determination of its DNA and surrounding sequence and expression of CPMO activity and protein in *E. coli*.

BRIEF DESCRIPTION OF THE DRAWINGS

FIG. 3 illustrates an alignment of the amino acid sequence of the CPMO of *Comamonas* sp. NCIMB 9872 with that of CHMO from *Acinetobacter* sp. NCIMB 9871 and a steroid monooxygenase (STMO) from *Rhodococcus rhodochrous*;

FIG. 5 illustrates CPMO-encoding gene, designated cpnB.

DETAILED DESCRIPTION OF THE PREFERRED EMBODIMENT

Cloning of the *Comamonas* sp. NCIMB 9872 CPMO-encoding Gene

Figure 2:
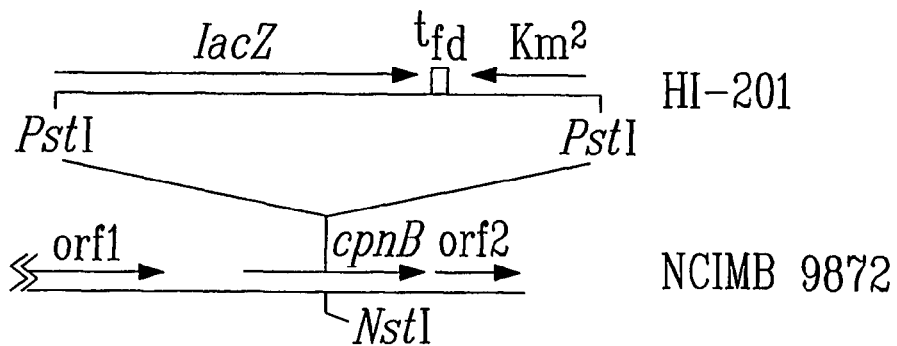
FIG. 2 illustrates the genetic organization in *Comamonas* sp. NCIMB 9872 in the SphI fragment containing cyclopentanone monooxygenase-encoding gene (cpnB) and additional open reading frames.

*Pseudomonas* sp. NCIMB 9872 (henceforth strain 9872) identified as a *Comamonas* by 16S rDNA sequencing in this study, was purchased from the National Collections of Industrial and Marine Bacteria Ltd (NCIMB, Aberdeen, Scotland) and grown at 30° C. in Luria-Bertani (LB) broth (Sambrook, J., et al., Molecular cloning: a laboratory manual, 2nd ed. Cold Spring Harbor Laboratory Press, Cold Spring Harbor, N.Y., 1989), or mineral salt medium (MSM), pH 7.0, containing 2 ml of cyclopentanone. The MSM recipe contains per liter: 1.0 g of $NH_4NO_3$, 1.5 g of $KH_2PO_4$, 1.5 g of $Na_2HPO_4$, 0.2 g $MgSO_4.7H_2O$, 0.01 g of $CaCl_2.2H_2O$, 0.005 of $FeSO.7H_2O$, 0.002 g of $MnSO_4.4H_2O$ and 0.1 g of yeast extract. Agar was added to 1.5% for plates. Genomic DNA of strain 9872 was prepared by the Marmur method (Marmur, J., *J. Mol. Biol.* 3: 208-218, 1961). At first, a Southern hybridization of DNA digested with BamHI was carried out using the *Acinetobacter* NCIMB 9871 CHMO-containing gene as probe. Since there was no positive result (hybridization conditions carried out at 65° C.) the CPMO protein was purified in order to obtain an N-terminal amino acid sequence. The purification of CPMO protein from cyclopentanone-grown cells was according to Griffin and Turgill (Griffin, M., et al., *Eur. J. Biochem.* 63:199-209, 1976). Using an automated protein sequencer (Perkin-Elmer model 477) a 40-residue amino-terminal sequence of the purified CPMO was obtained (FIG. 2). This sequence, longer by 11 amino acids, is in perfect agreement with that reported previously from the same organism (Willetts, A., *Trends in Biotech.* 15:55-62, 1997). Two degenerate oligodeoxynucleotide primers (5'-ACIACIATGA CIACNATGAC-3' (SEQ ID NO:1) and 5'-ARRTGRTAIA RYTGRTA-3' (SEQ ID NO:2), corresponding to amino acids 2-8 and 35-40, respectively) were synthesized to amplify a 116-bp product from total DNA prepared from strain 9872. The PCR amplification was performed in a Perkin Elmer-Model 2400 Thermal Cycler™ and the amplification conditions were 94° C. for 1 min, 50° C. for 1 min and 72° C. for 1 min for 30 cycles. The amplified product was cloned directly in the pXcmkn12 vector (Cha, J., et al., *Gene* 136, 369-370, 1993), transformed in *E. coli* JM109 and the resulting plasmid was designated pCMP10. Before using the amplified product as a gene probe its nucleotide sequence was confirmed. Nucleotide sequencing was determined by the Taq DyeDeoxy terminator cycle sequencing kit and the ABI Prism 310 Genetic Analyzer (Perkin Elmer). Plasmid isolation was performed by the method of Birnboim and Doly (Birnboim, H. C., and J. Doly, *DNA. Nucleic Acids Res.* 7:1513-1523, 1979).

In FIG. 2, Orf1 is most likely a transcriptional activator of the NtrC-type (Morett, E., L. Segovia, *J. Bacteriol.* 175:6067-6074, 1993). The amino acid sequence of ORF1 (C-terminal 391-amino acids) showed 38-40% identity to equivalent regions of proteins such as NTRC_ECOLI (Nitrogen regulation protein NR(I) from *E. coli*; Miranda, et al., *The complete nucleotide sequence of the glnALG operon of Eschericha coli K12* 15:2757-2770, 1987), ACOR_ALCEU (Acetoin catabolism regulatory protein from *Ralstonia eutropha*; Kruger, N., et al., *J. Bacteriol.* 179:4391-4400, 1992). The amino acid sequence of ORF2, showing similarity to enzymes of the short-chain alcohol dehydrogenase family (Jornvall, H., et al., *Biochemistry* 34: 6003-6013, 1995), is most homologous (45-46% identity) to a putative oxidoreductase CY39.16C of *Mycobacterium tuberculosis* (Swiss Prot sp:Q10855) and fadG3 of *M. tuberculosis* (GenBank accession number Z74025). For *Pseudomonas* sp. strain HI-201 the lacZ-Km$^r$ cassette from pKOK6.1 (Kokotek, W., et al., *Gene* 84: 467-471, 1989) was inserted into cpnB at the NsiI site.

In FIG. 2, the following terms are defined as follows: $t_{fd}$, transcriptional termination sequence of phage fd; Km$^r$, kanamycin resistance gene, lacZ, gene encoding b-galactosidase. Genes and markers are indicated with arrows.

To clone the CPMO-containing gene, the DNA insert from pCMP10 was amplified, labeled by the digoxigenin-11-UTP system according to manufacturer's instructions (Boehringer Mannheim GmbH) and used to probe a Southern hybridization of strain 9872 genomic DNA digested with various restriction enzymes (BamHI, EcoRI, HindIII, KpnI, NheI, PstI, SalI, SphI and XbaI). As a result, a single hybridizing band of ca 4.3-kb SphI fragment was obtained. Conditions of hybridization were as before. Subsequently, a purified 4.0- to 4.5-kb size fraction of SphI-cut total DNA separated on a 0.8% agarose gel was ligated to *E. coli* plasmid pUC18, which had been linearized and dephosphorylated. A clone containing the 4.3-kb insert was screened by colony hybridization using the PCR product as a probe; this recombinant plasmid was designated pCMP200.

DNA Sequence of the CPMO-encoding Gene (cpnB) and the Flanking Region

Nucleotide sequencing of the CPMO-encoding gene was initiated by using a primer designed from the sequence of the PCR product cloned in pCMP10 and further extended using oligonucleotides derived from the new sequence. Both DNA strands of the SphI fragment were sequenced and found to consist of 4281 base pairs (bp). The sequence was analyzed by GENETYX-Mac (Software Development Co., Ltd. Chiba, Japan) and the BLAST program (Altschul, S. F., et al., *Nucleic Acids Res.* 25:3389-3402, 1997). As a result three open reading frames (ORFs) arranged in the same direction were predicted (FIG. 2). The nucleotide sequence of the 1650-bp ORF encoding CPMO is preceded by a partial ORF1 (1173-bp) coding for the C-terminus of an NtrC-type transcriptional activator (Miranda, et al., *The complete nucleotide* sequence of the glnALG operon of Eschericha coli K12 15:2757-2770, 1987) and by a complete ORF2 (750-bp) coding for a homolog of the short-chain dehydrogenases/reductases (Jornvall, H., et al., *Biochemistry* 34: 6003-6013, 1995). The two intergenic regions are 244-bp and 32-bp, respectively. The CPMO-encoding gene is referred to cpnB (cyclopentanone and B designates the second step of the degradation pathway, see FIG. 1) hereafter. In FIG. 5, the CPMO-encoding gene starts at nucleotide position 1822 and ends 3471 that does not include the stop codon. Accordingly, the boundary of cpnA is 3507-4256. The partial open reading frame preceding cpnB is from 1-1174.

Figure 1:
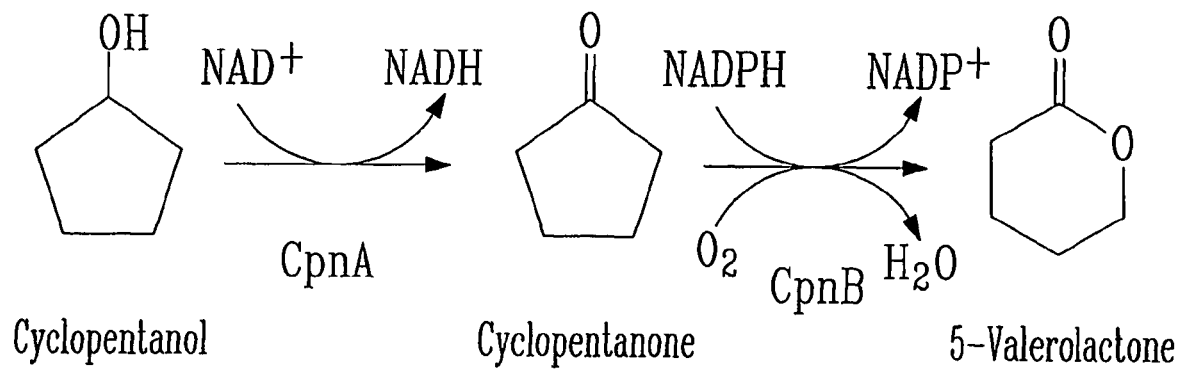
FIG. 1 illustrates the first two steps of cyclopentanol degradation by *Pseudomonas* sp. NCIMB 9872.

FIG. 1 has been adapted from Griffin, M., et al. (Griffin, M., et al., *Biochem. J.* 129:595-603, 1972). The designated genes are: cpnA encoding cyclopentanol dehydrogenase; cpnB encoding cyclopentanone 1,2-monooxygenase (CPMO). An alternative name for 5-valerolactone is 5-pentanolide. Subsequent reaction steps are the formation of 5-hydroxyvalerate, 5-oxovalerate, glutarate and finally acetyl CoA.

The amino acid sequence of the CPMO enzyme consists of 550 residues (FIG. 3). This sequence shows 36.5% identity and an additional 13.6% amino acid similarity with the 543-residue CHMO of *Acinetobacter* sp. strain NCIMB 9871. An equally related protein (549 amino acids; 37.3% identity and 12.4% similarity) is the putative steroid monooxygenase (STMO) of *Rhodococcus rhodochrous* (Morii, S., et al., GenBank accession number AB010439, 1998). The latter enzyme carries out the oxidation of progesterone to produce testosterone acetate. A CLUSTAL alignment of these three sequences gave 24.6% positional identity (FIG. 3).

In FIG. 3, asterisks indicate identical amino acids, dots indicated similar amino acids and dashes indicate gaps introduced to maximize the alignment. The amino-terminal peptide sequence confirmed by Edman degradation is underlined. The locations of the consensus FAD fingerprint sequences as described by Eppink et al. (Eppink, et al., *Prot. Sci.* 6:2454-2458, 1997) are as indicated. The conserved GD motif found in flavoprotein hydroxylases as a second FAD fingerprint is also indicated. Not shown is the DG motif of flavoprotein hydroxylases which has the sequence of chhhssDGxcSxhR. Lower case letters identify certain residues types: h, hydrophobic residues, s, small residues, c, charged residues, and x, any residues. Note that a DG doublet is present in CPMO and STMO sequence.

A notable sequence motif present in CPMO and related proteins is the FAD-binding fingerprint (GXGXXG) that is similar to those found in flavoprotein hydroxylases (Eppink, et al., *Prot. Sci.* 6:2454-2458, 1997). Flavoprotein hydroxylases (e.g. phenol hydroxylase, the structure is now known; Enroth, C., et al., *Structure* 6:605-617, 1998) are monooxygenases that catalyze the insertion of one atom of molecular oxygen into the substrate using NAD(P)H as electron donor. These proteins possess a conserved "Asp-Gly (DG)" motif for both FAD and NAD(P)H binding in between two fingerprint motifs for the FAD binding (fingerprint 1: GXGXXG; fingerprint 2: Gly-Asp [GD] motif). Sequence motifs in CPMO, STMO and CHMO differ from those in flavoprotein hydroxylases by having a repeated GXGXXG motif (amino acids 24 to 33 and 193 to 202 in CPMO numbering). The possibility that the second FAD fingerprint in CPMO and related proteins fulfils a dual role of FAD and NADPH binding awaits structural determination of a representative member of this family of proteins. It is reasonable to assume that a different mechanism in catalysis is reflected in the motifs seen in the two classes of proteins.

Expression of cpnB Gene in *E. coli*

Two primers of the following sequence were synthesized to amplify the cpnB gene and the resultant 1.7-kb DNA fragment was cloned in the pSD80 plasmid to yield pCMP201.

Plasmid pSD80 is a third generation derivative of the commercially available pKK223-3 vector (Pharmacia) that contains a tac promoter upstream of the multiple cloning site (MCS), an unc terminator sequence downstream of the MCS, and lacI$^q$ elsewhere on the plasmid (Smith, S. P., et al., *Biochemistry* 35:8805-8814, 1996). The primers were: 5'-AAA AGGCCTG AACTTCAATT ATTTAGGAGA C-3' (SEQ ID NO:3) and 5'-AAAACTGCAGGAGTTGCACA ACA-GAGTCTT AG-3' with built-in StuI and PstI restriction sites (underlined), respectively, to facilitate cloning at the compatible sites (SmaI and PstI) of the pSD80 vector. Vent DNA polymerase (New England BioLabs, Beverly, Mass.) was used and the amplification conditions were 94° C. for 1 min, 50° C. for 1 min, and 72° C. for 1 min, for 30 cycles. The amplified DNA fragment was purified from an agarose gel and digested with StuI and PstI. One of the resulting recombinant plasmids was designated pCMP201. By DNA sequencing it was established that no mutation had been introduced in the cpnB gene during PCR amplification.

Figure 4:
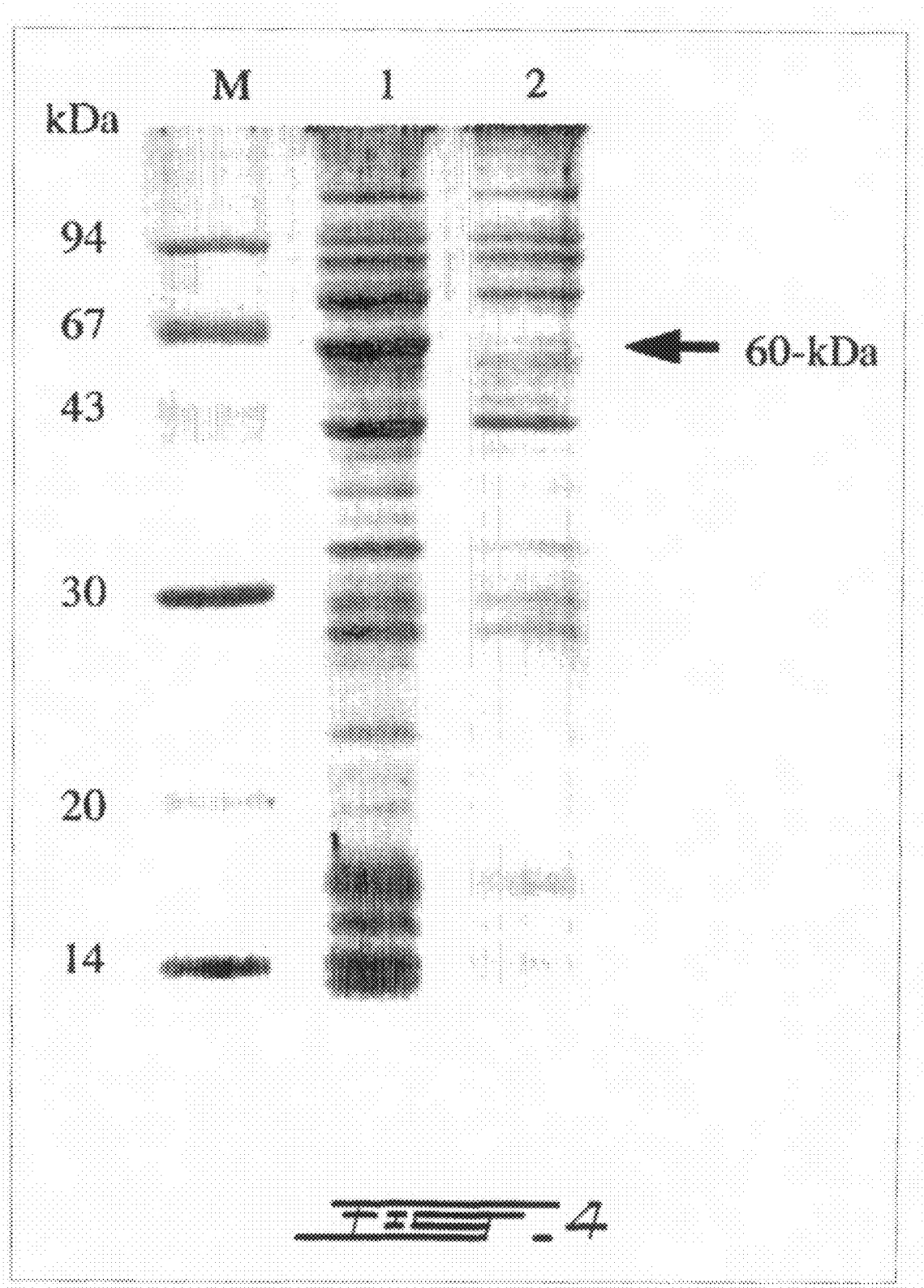
FIG. 4 illustrates a SDS-PAGE of crude extracts from *E. coli* (pCMP201)

FIG. 4 shows the production of a 60-kDa protein in a Coomassie blue-stained SDS-polyacrylamide gel of the crude protein extract prepared from *E. coli* JM109 (pCMP201) cells that were induced by 0.1 mM isopropyl-beta-D-thiogalactopyranoside (IPTG). The cells were induced at an absorbance (A600 nm) of 0.4 to 0.5 and the induction period was up to 4 hr. The observed molecular mass was in agreement with the predicted size of the 62-kDa CPMO. In the absence of IPTG, this protein band was not produced. Also, the CPMO enzyme activity was observed only in those cells grown in the presence of IPTG. CPMO activity was assayed at 25° C. by measuring a decrease in absorbance at 340 nm in 50 mM phosphate buffer (pH 7.8) containing 1 μmol of cyclopentanone, 0.2 μmol of NADPH, and the crude enzyme extract prepared from *E. coli* JM109 (pCMP201). These cells were cultivated in 100 ml of LB medium containing 100 μg/ml of ampicillin at 25° C. The IPTG-induced cells were harvested by centrifugation, washed in 50 mM phosphate buffer (pH 7.2), resuspended in 1/20 volume of same buffer, and sonicated by four-20 sec bursts with a Braun-Sonifier™ 250 apparatus. After centrifugation for 30 min at 18,000×g and at 4° C., the supernatant was used for determination of enzyme activity. One unit (U) of activity is defined as the amount of enzyme required to convert 1 μmol of substrate in 1 min. Protein concentration was determined by the method of Bradford (Bradford, M. M., *Anal. Biochem.* 72: 248-254, 1976). As a result the specific activity of the CPMO enzyme was found to be 0.28 U/mg. The specific activity of CPMO in the native *Pseudomonas* was reported to be 0.11 U/mg (Griffin, M., et al., *Biochem. J.* 129:595-603, 1972).

In FIG. 4, lane 1 has been loaded with extracts of IPTG-induced *E. coli* and lane 2 has been loaded with extracts of *E. coli* in absence of IPTG. M means molecular weight markers as indicated in kilo daltons. The arrow indicates the production of the desired 60-kDa protein.

Inactivation of cpnB Gene

*Pseudomonas* sp. strain HI-201 was constructed by chromosomal inactivation of the cpnB gene using a lacZ-Km$^r$ cassette from the mobilizable pKOK6.1 vector (Kokotek, W., et al., *Gene* 84: 467-471, 1989). In pKOK6.1 the lacZ gene is promoterless and in addition to Km$^r$ it is ampicillin resistant (Ap$^r$). The lacZ-Km$^r$ cassette was excised as a PstI-fragment and inserted into the NsiI site within the cpnB gene in pCMP200, yielding pCMP202. Electroporation of this plasmid into 9872 cells was carried out in the Gene Pulser™ (BioRads) and the parameters of electroporation were 2.5 kV, 25 uF and 200 ohm. The cells were initially washed with 1 mM HEPES buffer and resuspended in 1 mM HEPES containing 10% glycerol. Km$^r$ colonies were selected on LB plates containing Km (250 μg/ml). To select for double crossover mutants, a second screening on LB plates containing Ap (300 μg/ml) was carried out. The inactivation of cpnB (FIG. 2), was confirmed by PCR. The resulting mutant HI-201 was found not to be able to grow on cyclopentanol or cyclopentanone as a sole carbon and energy source. This result indicated that cpnB is essential for the degradation of cyclopentanol and it appeared that there was only one copy of the cpnB gene in strain 9872.

As expected of a flavoprotein the amino acid sequence of CPMO contains motifs of FAD fingerprints similar to those found in flavoprotein hydroxylases.

Nucleotide Sequence Accession Number

The DNA sequence of the 4,281-bp SphI fragment has been submitted to DDBJ and assigned accession number AB022102. The release of this data awaits the inventors' authorization.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A recombinant cyclopentanone monooxygenase (CPMO) having:
   (a) the amino acid sequence as set forth in SEQ ID NO: 5; or
   (b) the amino acid sequence encoded by the nucleic acid sequence as set forth in SEQ ID NO: 8.

2. The recombinant cyclopentanone monooxygenase (CPMO) of claim 1, wherein said CPMO has an enzymatic activity higher than 0.28 U/mg.

3. The recombinant cyclopentanone monooxygenase (CPMO) of claim 1, wherein said CPMO is prepared from *Comamonas* sp. NCIMB 9872.

4. The recombinant cyclopentanone monooxygenase (CPMO) of claim 1, wherein said CPMO has the sequence as set forth in SEQ ID NO: 5.

* * * * *

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Primers for Comamonas sp.
<220> FEATURE:
<221> NAME/KEY: modified_base
<222> LOCATION: (3)...(3)
<223> OTHER INFORMATION: I
<220> FEATURE:
<221> NAME/KEY: modified_base
<222> LOCATION: (6)...(6)
<223> OTHER INFORMATION: I
<220> FEATURE:
<221> NAME/KEY: modified_base
<222> LOCATION: (12)...(12)
<223> OTHER INFORMATION: I
<220> FEATURE:
<221> NAME/KEY: unsure
<222> LOCATION: (15)...(15)
<223> OTHER INFORMATION: N = any base

<400> SEQUENCE: 1
acnacnatga cnacnatgac                                              20

<210> SEQ ID NO 2
<211> LENGTH: 17
<212> TYPE: DNA
<213> ORGANISM: Artificial Sequence
<220> FEATURE:
<223> OTHER INFORMATION: Primers for Comamonas sp.
<220> FEATURE:
<221> NAME/KEY: modified_base
<222> LOCATION: (9)...(9)
<223> OTHER INFORMATION: I

<400> SEQUENCE: 2
arrtgrtana rytgrta                                                 17

<210> SEQ ID NO 3
<211> LENGTH: 31
<212> TYPE: DNA
<213> ORGANISM: Artificial Sequence
<220> FEATURE:
<223> OTHER INFORMATION: Primers for Comamonas sp.

<400> SEQUENCE: 3
aaaaggcctg aacttcaatt atttaggaga c                                 31
```

<210> SEQ ID NO 4
<211> LENGTH: 32
<212> TYPE: DNA
<213> ORGANISM: Artificial Sequence
<220> FEATURE:
<223> OTHER INFORMATION: Primers for Comamonas sp.

<400> SEQUENCE: 4
aaaactgcag gagttgcaca acagagtctt ag                          32

<210> SEQ ID NO 5
<211> LENGTH: 550
<212> TYPE: PRT
<213> ORGANISM: Comamonas sp

<400> SEQUENCE: 5

```
Met Thr Thr Met Thr Thr Met Thr Thr Glu Gln Leu Gly Met Asn Asn
 1               5                  10                  15

Ser Val Asn Asp Lys Leu Asp Val Leu Leu Ile Gly Ala Gly Phe Thr
            20                  25                  30

Gly Leu Tyr Gln Leu Tyr His Leu Arg Lys Leu Gly Tyr Lys Val His
        35                  40                  45

Leu Val Asp Ala Gly Ala Asp Ile Gly Gly Ile Trp His Trp Asn Cys
50                  55                  60

Tyr Pro Gly Ala Arg Val Asp Thr His Cys Gln Ile Tyr Gln Tyr Ser
65                  70                  75                  80

Ile Pro Glu Leu Trp Gln Glu Phe Asn Trp Lys Glu Leu Phe Pro Asn
                85                  90                  95

Trp Ala Gln Met Arg Glu Tyr Phe His Phe Ala Asp Lys Lys Leu Asp
            100                 105                 110

Leu Ser Lys Asp Ile Ser Phe Asn Thr Arg Val Gln Ser Ala Val Phe
        115                 120                 125

Asp Glu Gly Thr Arg Glu Trp Thr Val Arg Ser Ile Gly His Gln Pro
    130                 135                 140

Ile Gln Ala Arg Phe Val Ile Ala Asn Leu Gly Phe Gly Ala Ser Pro
145                 150                 155                 160

Ser Thr Pro Asn Val Asp Gly Ile Glu Thr Phe Lys Gly Gln Trp Tyr
                165                 170                 175

His Thr Ala Leu Trp Pro Gln Glu Gly Val Asn Met Ala Gly Lys Arg
            180                 185                 190

Val Ala Ile Ile Gly Thr Gly Ser Ser Gly Val Gln Val Ala Gln Glu
        195                 200                 205

Ala Ala Leu Asp Ala Lys Gln Val Thr Val Tyr Gln Arg Thr Pro Asn
    210                 215                 220

Leu Ala Leu Pro Met His Gln Lys Gln Leu Ser Ala Glu Asp Asn Leu
225                 230                 235                 240

Arg Met Lys Pro Glu Leu Pro Ala Ala Phe Glu Arg Arg Gly Lys Cys
                245                 250                 255

Phe Ala Gly Phe Asp Phe Asp Phe Ile Ala Lys Asn Ala Thr Glu Leu
            260                 265                 270

Ser Ala Ala Glu Arg Thr Glu Ile Leu Glu Glu Leu Trp Asn Ala Gly
        275                 280                 285

Gly Phe Arg Tyr Trp Leu Ala Asn Phe Gln Asp Tyr Leu Phe Asp Asp
    290                 295                 300

Lys Ala Asn Asp Tyr Val Tyr Glu Phe Trp Arg Asp Lys Val Arg Ala
305                 310                 315                 320
```

```
Arg Ile Lys Asp Pro Lys Val Ala Glu Lys Leu Ala Pro Met Lys Lys
            325                 330                 335

Pro His Pro Tyr Gly Ala Lys Arg Pro Ser Leu Glu Gln Trp Tyr Tyr
            340                 345                 350

Glu Ile Phe Asn Gln Asn Asn Val Thr Leu Val Asp Val Asn Glu Thr
            355                 360                 365

Pro Val Leu Arg Ile Thr Glu Lys Gly Ile Val Thr Ala Glu Gly Glu
370                 375                 380

Ala Glu Phe Asp Leu Ile Val Phe Ala Thr Gly Phe Asp Ala Val Thr
385                 390                 395                 400

Gly Gly Leu Thr Ser Ile Asp Phe Arg Asn Asn Gln Gly Gln Ser Phe
            405                 410                 415

Lys Asp Val Trp Ser Asp Gly Ile Arg Thr Gln Leu Gly Val Ala Thr
            420                 425                 430

Ala Gly Phe Pro Asn Leu Leu Phe Gly Tyr Gly Pro Gln Ser Pro Ala
            435                 440                 445

Gly Phe Cys Asn Gly Pro Ser Ser Ala Glu Tyr Gln Gly Asp Leu Leu
        450                 455                 460

Ile Gln Leu Met Asn Tyr Leu Arg Asp Asn Asn Ile Ser Arg Ile Glu
465                 470                 475                 480

Ala Gln Ser Glu Ala Gln Glu Glu Trp Ser Lys Leu Ile Ala Asp Phe
            485                 490                 495

Trp Asp Ser Ser Leu Phe Pro Arg Ala Lys Ser Trp Tyr Gln Gly Ser
            500                 505                 510

Asn Ile Pro Gly Lys Lys Val Glu Ser Leu Asn Phe Pro Leu Gly Leu
            515                 520                 525

Pro Thr Tyr Ile Ser Lys Phe Asn Glu Ser Ala Glu Lys Gly Tyr Ala
            530                 535                 540

Gly Phe Ser Leu Ala Ser
545                 550

<210> SEQ ID NO 6
<211> LENGTH: 549
<212> TYPE: PRT
<213> ORGANISM: Rhodococcus rhodochrous

<400> SEQUENCE: 6

Met Asn Gly Gln His Pro Arg Ser Val Val Thr Ala Pro Asp Ala Thr
1               5                   10                  15

Thr Gly Thr Thr Ser Tyr Asp Val Val Val Gly Ala Gly Ile Ala
            20                  25                  30

Gly Leu Tyr Ala Ile His Arg Phe Arg Ser Gln Gly Leu Thr Val Arg
            35                  40                  45

Ala Phe Glu Ala Ala Ser Gly Val Gly Gly Val Trp Tyr Trp Asn Arg
50                  55                  60

Tyr Pro Gly Ala Arg Cys Asp Val Glu Ser Ile Asp Tyr Ser Tyr Ser
65                  70                  75                  80

Phe Ser Pro Glu Leu Glu Gln Glu Trp Asn Trp Ser Glu Lys Tyr Ala
            85                  90                  95

Thr Gln Pro Glu Ile Leu Ala Tyr Leu Glu His Val Ala Asp Arg Phe
            100                 105                 110

Asp Leu Arg Arg Asp Ile Arg Phe Asp Thr Arg Val Thr Ser Ala Val
            115                 120                 125

Leu Asp Glu Glu Gly Leu Arg Trp Thr Val Arg Thr Asp Arg Gly Asp
130                 135                 140
```

-continued

```
Glu Val Ser Ala Arg Phe Leu Val Val Ala Ala Gly Pro Leu Ser Asn
145                 150                 155                 160

Ala Asn Thr Pro Ala Phe Asp Gly Leu Asp Arg Phe Thr Gly Asp Ile
                165                 170                 175

Val His Thr Ala Arg Trp Pro His Asp Gly Val Asp Phe Thr Gly Lys
            180                 185                 190

Arg Val Gly Val Ile Gly Thr Gly Ser Ser Gly Ile Gln Ser Ile Pro
        195                 200                 205

Ile Ile Ala Glu Gln Ala Glu Gln Leu Phe Val Phe Gln Arg Ser Ala
    210                 215                 220

Asn Tyr Ser Ile Pro Ala Gly Asn Val Pro Leu Asp Asp Ala Thr Arg
225                 230                 235                 240

Ala Glu Gln Lys Ala Asn Tyr Ala Glu Arg Arg Leu Ser Arg Glu
                245                 250                 255

Ser Gly Gly Gly Ser Pro His Arg Pro His Pro Lys Ser Ala Leu Glu
                260                 265                 270

Val Ser Glu Glu Glu Arg Arg Ala Val Tyr Glu Glu Arg Trp Lys Leu
            275                 280                 285

Gly Gly Val Leu Phe Ser Lys Ala Phe Pro Asp Gln Leu Thr Asp Pro
        290                 295                 300

Ala Ala Asn Asp Thr Ala Arg Ala Phe Trp Glu Glu Lys Ile Arg Ala
305                 310                 315                 320

Val Val Asp Asp Pro Ala Val Ala Glu Leu Leu Thr Pro Lys Asp His
                325                 330                 335

Ala Ile Gly Ala Lys Arg Ile Val Thr Asp Ser Gly Tyr Tyr Glu Thr
            340                 345                 350

Tyr Asn Arg Asp Asn Val Glu Leu Val Asp Leu Arg Ser Thr Pro Ile
        355                 360                 365

Val Gly Met Asp Glu Thr Gly Ile Val Thr Thr Gly Ala His Tyr Asp
    370                 375                 380

Leu Asp Met Ile Val Leu Ala Thr Gly Phe Asp Ala Met Thr Gly Ser
385                 390                 395                 400

Leu Asp Lys Leu Glu Ile Val Gly Arg Gly Arg Thr Leu Lys Glu
                405                 410                 415

Thr Trp Ala Ala Gly Pro Arg Thr Tyr Leu Gly Leu Gly Ile Asp Gly
                420                 425                 430

Phe Pro Asn Phe Phe Asn Leu Thr Gly Pro Gly Ser Pro Ser Val Leu
        435                 440                 445

Ala Asn Met Val Leu His Ser Glu Leu His Val Asp Trp Val Ala Asp
450                 455                 460

Ala Ile Ala Tyr Leu Asp Ala Arg Gly Ala Ala Gly Ile Glu Gly Thr
465                 470                 475                 480

Pro Glu Ala Val Ala Asp Trp Val Glu Glu Cys Arg Asn Arg Ala Glu
                485                 490                 495

Ala Ser Leu Leu Asn Ser Ala Asn Ser Trp Tyr Leu Gly Ala Asn Ile
            500                 505                 510

Pro Gly Arg Pro Arg Val Phe Met Pro Phe Leu Gly Gly Phe Gly Val
        515                 520                 525

Tyr Arg Glu Ile Ile Thr Glu Val Ala Glu Ser Gly Tyr Lys Gly Phe
    530                 535                 540

Ala Ile Leu Glu Gly
545
```

<210> SEQ ID NO 7
<211> LENGTH: 543
<212> TYPE: PRT
<213> ORGANISM: Acinetobacter sp

<400> SEQUENCE: 7

```
Met Ser Gln Lys Met Asp Phe Asp Ala Ile Val Ile Gly Gly Gly Phe
1               5                   10                  15

Gly Gly Leu Tyr Ala Val Lys Lys Leu Arg Asp Glu Leu Glu Leu Lys
            20                  25                  30

Val Gln Ala Phe Asp Lys Ala Thr Asp Val Ala Gly Thr Trp Tyr Trp
        35                  40                  45

Asn Arg Tyr Pro Gly Ala Leu Thr Asp Thr Glu Thr His Leu Tyr Cys
    50                  55                  60

Tyr Ser Trp Asp Lys Glu Leu Leu Gln Ser Leu Glu Ile Lys Lys Lys
65                  70                  75                  80

Tyr Val Gln Gly Pro Asp Val Arg Lys Tyr Leu Gln Gln Val Ala Glu
                85                  90                  95

Lys His Asp Leu Lys Lys Ser Tyr Gln Phe Asn Thr Ala Val Gln Ser
            100                 105                 110

Ala His Tyr Asn Glu Ala Asp Ala Leu Trp Glu Val Thr Thr Glu Tyr
        115                 120                 125

Gly Asp Lys Tyr Thr Ala Arg Phe Leu Ile Thr Ala Leu Gly Leu Leu
    130                 135                 140

Ser Ala Pro Asn Leu Pro Asn Ile Lys Gly Ile Asn Gln Phe Lys Gly
145                 150                 155                 160

Glu Leu His His Thr Ser Arg Trp Pro Asp Asp Val Ser Phe Glu Gly
                165                 170                 175

Lys Arg Val Gly Val Ile Gly Thr Gly Ser Thr Gly Val Gln Val Ile
            180                 185                 190

Thr Ala Val Ala Pro Leu Ala Lys His Leu Thr Val Phe Gln Arg Ser
        195                 200                 205

Ala Gln Tyr Ser Val Pro Ile Gly Asn Asp Pro Leu Ser Glu Glu Asp
    210                 215                 220

Val Lys Lys Ile Lys Asp Asn Tyr Asp Lys Ser Leu Gly Trp Cys Met
225                 230                 235                 240

Asn Ser Ala Leu Ala Phe Ala Leu Asn Glu Ser Thr Val Pro Ala Met
                245                 250                 255

Ser Val Ser Ala Glu Glu Arg Lys Ala Val Phe Glu Lys Ala Trp Gln
            260                 265                 270

Thr Gly Gly Gly Phe Arg Phe Met Phe Glu Thr Phe Gly Asp Ile Ala
        275                 280                 285

Thr Asn Met Glu Ala Asn Ile Glu Ala Gln Asn Phe Ile Lys Gly Lys
    290                 295                 300

Ile Ala Glu Ile Val Lys Asp Pro Ala Ile Ala Gln Lys Leu Met Pro
305                 310                 315                 320

Gln Asp Leu Tyr Ala Lys Arg Pro Leu Cys Asp Ser Gly Tyr Tyr Asn
                325                 330                 335

Thr Phe Asn Arg Asp Asn Val Arg Leu Glu Asp Val Lys Ala Asn Pro
            340                 345                 350

Ile Val Glu Ile Thr Glu Asn Gly Val Lys Leu Glu Asn Gly Asp Phe
        355                 360                 365

Val Glu Leu Asp Met Leu Ile Cys Ala Thr Gly Phe Asp Ala Val Asp
    370                 375                 380
```

-continued

```
Gly Asn Tyr Val Arg Met Asp Ile Gln Gly Lys Asn Gly Leu Ala Met
385                 390                 395                 400

Lys Asp Tyr Trp Lys Glu Gly Pro Ser Ser Tyr Met Gly Val Thr Val
            405                 410                 415

Asn Asn Tyr Pro Asn Met Phe Met Val Leu Gly Pro Asn Gly Pro Phe
        420                 425                 430

Thr Asn Leu Pro Pro Ser Ile Glu Ser Gln Val Glu Trp Ile Ser Asp
    435                 440                 445

Thr Ile Gln Tyr Thr Val Glu Asn Asn Val Glu Ser Ile Glu Ala Thr
450                 455                 460

Lys Glu Ala Glu Glu Gln Trp Thr Gln Thr Cys Ala Asn Ile Ala Glu
465                 470                 475                 480

Met Thr Leu Phe Pro Lys Ala Gln Ser Trp Ile Phe Gly Ala Asn Ile
            485                 490                 495

Pro Gly Lys Lys Asn Thr Val Tyr Phe Tyr Leu Gly Gly Leu Lys Glu
        500                 505                 510

Tyr Arg Thr Cys Ala Ser Asn Cys Lys Asn His Ala Tyr Glu Gly Phe
    515                 520                 525

Asp Ile Gln Leu Gln Arg Ser Asp Ile Lys Gln Pro Ala Asn Ala
530                 535                 540
```

<210> SEQ ID NO 8
<211> LENGTH: 4281
<212> TYPE: DNA
<213> ORGANISM: Comamonas sp
<220> FEATURE:
<221> NAME/KEY: CDS
<222> LOCATION: (1822)...(3471)

<400> SEQUENCE: 8

```
gcatgcgata gcggcacgtt ggtgggcggg cgagcgcggc cacgagcgcg tctctcgctc      60
caccgacatc acatcgccgg tcaccggcga gaacattggc aagatcctgc gcttttcgcc     120
gctgaagccg cagggctacg agagaatttt tcagtccggc ctggcggact cgacccagca     180
cacccccagg atggtgcgtt tcggacagtt cctgtcctgt gatccagaga ccatcaacac     240
cctggagaca ttggagcgga tcgcgcgcgc cgacgtcaat gtcttgctgc atggagagac     300
gggcacgggc aaagagctga tagctcgcca cattcatgtc gcgagccgcc ggcgggatgc     360
gccctacctc gccatcaact gcggggcaat cagctcggag ttgctggaga gtactttttt     420
tggctatgtg cgcggagcat tctccggggc agatcccaag gccgcgccg ctactttga      480
atcggtgggc gaaggcacct tgtttctgga cgagatcggc gagctgccct tggccatgca     540
ggcggcattg ttgcgcgtgc tggaagacgg aagcttttctg cgtgtgggct catcgacccc     600
gcagcgcgcc tcgtgccgca ttatcgcggc cacgcaccgc aatctggagg aactcatcgc     660
acagggcctg tttcgccagg atctctacta ccgtctcaag atcgttcaga aaaggctcaa     720
gccgatacgg gaacgcacct gtgacatcgc cttgctggca gagcaattca aatctgcact     780
ggcgcaaaag caccagatcc cgaacgtgca gatccacccc gaggccatgg cagtcatgga     840
gcgctaccag tggccgggca atgcgcgcga atccgcaat gtgatggaag ccgccctgat     900
ctgctccgat ggtgaaatca cgctcgccag cctgccccg gaagtatctg agaactccac     960
ctatcctctg caaagccggg tggccgaagc gaatagcgag atgcctcccg tctccggcaa    1020
cgactatgaa cggcaactca tcgtgggttt gctgcgcaag taccgaaagg tcaatcatgt    1080
ggcgagggcc ctgggcctcg cgcgctccac gctctatcgg aaattcgcag acttgggcat    1140
```

```
tgaccaacgc gagtatgtca atgatctgtc cgattaacac tgctgcgccc tgcgcttgcg    1200
gcaacgcagt atcgtcggaa cgcgggcaac gctaaaggca gccgccgtcg gcatcggttg    1260
ccgcccggtg ttgttttgtcg gctgagaccg cctgcagcac cagcccctcc attcctcgtg    1320
tctagatctc cttgcaacgc tgtcacagcg tgcttttttc gtggcgcggg acttctcgcg    1380
atgagggcct gcaagggcgg cgcatcaaaa caagcgccct gtcctcagga cgtttgcgcc    1440
gtcgctggct atgggcagtc tgcatgatcc gcttgggctt gcccaccatg cgcgcgactg    1500
cgctctttcc tgttgggcgc atcgtcatcc cgaccttcct gaaatccatt tccacagggc    1560
cggcctgagc cagacagcga tcggcaggct ctcgcatctc ggacagtggt gcgctacacc    1620
acaggacaca agtgtccggc gcgtggcacg cagcggcctt tgctgcgcac gatgcgtgct    1680
tttggcacat ggaaaccctc ggttttccg aaccagagac ctggcacaag tcttgataac    1740
tcctgagtga ctgatgcaac gcatctcagt ccgggagcgt ggacgacacg ccctgaact    1800 tcaattattt aggagaccca t atg acc acc atg acc acc atg acc acc gaa    1851
              Met Thr Thr Met Thr Thr Met Thr Thr Glu
              1               5                   10 caa ctc ggc atg aac aac tct gtc aat gac aag ctt gac gtt ttg ctc    1899
Gln Leu Gly Met Asn Asn Ser Val Asn Asp Lys Leu Asp Val Leu Leu
             15                  20                  25 atc ggc gcc ggc ttc acc ggt ctc tac cag ctc tat cac ctg cgc aag    1947
Ile Gly Ala Gly Phe Thr Gly Leu Tyr Gln Leu Tyr His Leu Arg Lys
         30                  35                  40 ctg ggc tac aag gtt cat ctc gtc gac gcc ggt gcc gat att ggc ggg    1995
Leu Gly Tyr Lys Val His Leu Val Asp Ala Gly Ala Asp Ile Gly Gly
     45                  50                  55 atc tgg cat tgg aac tgc tac ccc gga gcg cgt gtg gat acc cac tgc    2043
Ile Trp His Trp Asn Cys Tyr Pro Gly Ala Arg Val Asp Thr His Cys
 60                  65                  70 cag atc tac cag tac tcc att cca gag ttg tgg cag gag ttc aac tgg    2091
Gln Ile Tyr Gln Tyr Ser Ile Pro Glu Leu Trp Gln Glu Phe Asn Trp
 75                  80                  85                  90 aaa gag ctg ttc cct aac tgg gcg caa atg cgc gag tat ttc cat ttt    2139
Lys Glu Leu Phe Pro Asn Trp Ala Gln Met Arg Glu Tyr Phe His Phe
                 95                 100                 105 gcc gac aag aag ctc gac ctg agc aag gac atc agc ttc aac acc cgt    2187
Ala Asp Lys Lys Leu Asp Leu Ser Lys Asp Ile Ser Phe Asn Thr Arg
             110                 115                 120 gtg cag tcg gcc gtc ttt gac gaa ggc aca cgc gaa tgg acg gta cgc    2235
Val Gln Ser Ala Val Phe Asp Glu Gly Thr Arg Glu Trp Thr Val Arg
         125                 130                 135 tcg atc gga cac cag ccg atc cag gcc agg ttc gtc atc gcc aac ctt    2283
Ser Ile Gly His Gln Pro Ile Gln Ala Arg Phe Val Ile Ala Asn Leu
     140                 145                 150 ggc ttc ggt gcc agc ccc agc acg ccc aat gtc gat ggc atc gag aca    2331
Gly Phe Gly Ala Ser Pro Ser Thr Pro Asn Val Asp Gly Ile Glu Thr
155                 160                 165                 170 ttc aaa ggc cag tgg tat cac act gct ctg tgg ccc cag gaa ggc gtg    2379
Phe Lys Gly Gln Trp Tyr His Thr Ala Leu Trp Pro Gln Glu Gly Val
                 175                 180                 185 aac atg gcc ggc aag cgc gtg gcc atc att ggc acc ggc tcc agc ggg    2427
Asn Met Ala Gly Lys Arg Val Ala Ile Ile Gly Thr Gly Ser Ser Gly
             190                 195                 200 gtc cag gtc gcc cag gag gct gcc ctt gat gcg aaa cag gtg acg gtg    2475
Val Gln Val Ala Gln Glu Ala Ala Leu Asp Ala Lys Gln Val Thr Val
         205                 210                 215
```

-continued

| | |
|---|---|
| tac cag cgc acc ccc aac ctg gcc ttg ccc atg cat cag aag cag ctc<br>Tyr Gln Arg Thr Pro Asn Leu Ala Leu Pro Met His Gln Lys Gln Leu<br>220                           225                      230 | 2523 |
| agc gcc gag gac aat ctg cgc atg aag ccc gag ctt ccc gca gcg ttc<br>Ser Ala Glu Asp Asn Leu Arg Met Lys Pro Glu Leu Pro Ala Ala Phe<br>235                         240                     245                 250 | 2571 |
| gag aga cgc ggc aag tgc ttc gcc ggc ttc gac ttc gac ttc atc gcc<br>Glu Arg Arg Gly Lys Cys Phe Ala Gly Phe Asp Phe Asp Phe Ile Ala<br>                     255                     260                 265 | 2619 |
| aag aac gcg acc gag ctg tcc gct gcg gag cgc aca gag atc ttg gaa<br>Lys Asn Ala Thr Glu Leu Ser Ala Ala Glu Arg Thr Glu Ile Leu Glu<br>         270                     275                     280 | 2667 |
| gag ctg tgg aac gcc ggc ggc ttc cgc tac tgg ctg gcc aat ttc caa<br>Glu Leu Trp Asn Ala Gly Gly Phe Arg Tyr Trp Leu Ala Asn Phe Gln<br>         285                     290                     295 | 2715 |
| gac tat ctg ttc gat gac aag gcc aac gat tac gtc tac gag ttc tgg<br>Asp Tyr Leu Phe Asp Asp Lys Ala Asn Asp Tyr Val Tyr Glu Phe Trp<br>300                         305                     310 | 2763 |
| cgc gac aag gtc cgc gcc cgc atc aag gat ccg aaa gtt gcc gag aag<br>Arg Asp Lys Val Arg Ala Arg Ile Lys Asp Pro Lys Val Ala Glu Lys<br>315                         320                     325                 330 | 2811 |
| ctc gcc ccc atg aag aag ccg cat cct tac gga gcc aag cgc cct tcg<br>Leu Ala Pro Met Lys Lys Pro His Pro Tyr Gly Ala Lys Arg Pro Ser<br>                  335                     340                     345 | 2859 |
| ctg gag cag tgg tac tac gag atc ttc aat cag aac aac gtc acg ctg<br>Leu Glu Gln Trp Tyr Tyr Glu Ile Phe Asn Gln Asn Asn Val Thr Leu<br>               350                     355                     360 | 2907 |
| gtg gat gtc aac gaa aca ccg gtg ctt cgc atc acc gag aaa ggc atc<br>Val Asp Val Asn Glu Thr Pro Val Leu Arg Ile Thr Glu Lys Gly Ile<br>         365                     370                     375 | 2955 |
| gtg acc gct gag ggt gaa gcc gaa ttc gac ctg atc gtg ttc gcg acc<br>Val Thr Ala Glu Gly Glu Ala Glu Phe Asp Leu Ile Val Phe Ala Thr<br>380                         385                     390 | 3003 |
| ggc ttc gac gca gtg acc ggg gga ctc acc agc atc gac ttc cgc aac<br>Gly Phe Asp Ala Val Thr Gly Gly Leu Thr Ser Ile Asp Phe Arg Asn<br>395                         400                     405                 410 | 3051 |
| aac cag ggc cag agc ttc aag gat gtg tgg tct gac gga atc cgc acc<br>Asn Gln Gly Gln Ser Phe Lys Asp Val Trp Ser Asp Gly Ile Arg Thr<br>               415                     420                     425 | 3099 |
| cag ctg gga gtg gcc acg gca ggt ttt ccc aac ttg ctc ttt ggc tac<br>Gln Leu Gly Val Ala Thr Ala Gly Phe Pro Asn Leu Leu Phe Gly Tyr<br>         430                     435                     440 | 3147 |
| gga cct caa tcg cct gcg ggc ttc tgc aac ggt ccg tcg agc gcc gaa<br>Gly Pro Gln Ser Pro Ala Gly Phe Cys Asn Gly Pro Ser Ser Ala Glu<br>         445                     450                     455 | 3195 |
| tac cag ggc gat ctg ctg atc cag ctg atg aac tac cta cgc gac aac<br>Tyr Gln Gly Asp Leu Leu Ile Gln Leu Met Asn Tyr Leu Arg Asp Asn<br>460                         465                     470 | 3243 |
| aac atc tcg cgc atc gaa gcc cag tcc gag gca cag gaa gaa tgg agc<br>Asn Ile Ser Arg Ile Glu Ala Gln Ser Glu Ala Gln Glu Glu Trp Ser<br>475                         480                     485                 490 | 3291 |
| aag ctg atc gca gac ttc tgg gac agc tcg ctg ttc ccc cgc gca aag<br>Lys Leu Ile Ala Asp Phe Trp Asp Ser Ser Leu Phe Pro Arg Ala Lys<br>               495                     500                     505 | 3339 |
| tcc tgg tac caa gga tcc aac atc ccg ggc aag aaa gtc gag agc ctg<br>Ser Trp Tyr Gln Gly Ser Asn Ile Pro Gly Lys Lys Val Glu Ser Leu<br>         510                     515                     520 | 3387 |
| aac ttc ccg ctg ggg ctg cca acc tat ata tcc aaa ttc aat gaa agc<br>Asn Phe Pro Leu Gly Leu Pro Thr Tyr Ile Ser Lys Phe Asn Glu Ser<br>525                         530                     535 | 3435 |

```
gct gaa aaa gga tat gca ggc ttc tcg ctg gcc agc taagactctg                  3481
Ala Glu Lys Gly Tyr Ala Gly Phe Ser Leu Ala Ser
    540                 545                 550 ttgtgcaact cctggagaca agcatatggg acgtgtaaat gacaaagtgg ttctcgtcac           3541
tggcggtgcc atgggaatgg gcctgaccca ttgcaccttg ctggcccgcg aggggggccac          3601 cgtttacctc agcgacatga atgaggaact gggccaccaa gccgtagcgg agatccgtcg           3661
gcaaggtggc aaggcccact tcctgcacct ggacgtgacc aacgagaatc actggacagg           3721
tgccgtggac accatcctcg ccgagtccga ccggctggac gcgctggtca acaacgccgg           3781
cattttgacc ctcaaacccg ttcaggacac cagcaacgaa gaatgggatc gcatctttga           3841
aatcaatgtc cgcagtgtgt tcttgggcac gcgagcagtg atcgagccca tgcgtaaagc           3901
ccataaaggc tgcatcgtca atgtgtcgtc catctacggt ctggtgggtg cgccgggagc           3961
tgcggcctac gaggcctcca aaggtgccgt gcgcttgttt accaaggctt gcgcggtgga           4021
cctggcaccg ttcaatattc gggtcaactc ggtccaccca ggggtgatcg caacacccat           4081
gacgcagcag atcctggacg ccccacagag cgcacgtgcg cttctgggcc ccacgctgct           4141
gggtcgtgcg gcccagccga tggaggtctc ccaggcggtg cttttcctgg tctcggacga           4201
ggcctcgttc gtgcatggct ctgaactcgt cgtcgacgga gggtatacgg cgaactgaga           4261
aaggaacatc ctcggcatgc                                                       4281
```